US010779881B2

(12) United States Patent
Twomey

(10) Patent No.: US 10,779,881 B2
(45) Date of Patent: Sep. 22, 2020

(54) SURGICAL INSTRUMENTS AND METHODS FOR PERFORMING TONSILLECTOMY AND ADENOIDECTOMY PROCEDURES

(71) Applicant: COVIDIEN LP, Mansfield, MA (US)

(72) Inventor: John R. Twomey, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/043,575

(22) Filed: Jul. 24, 2018

(65) Prior Publication Data
US 2018/0325584 A1 Nov. 15, 2018

Related U.S. Application Data

(63) Continuation of application No. 14/738,201, filed on Jun. 12, 2015, now Pat. No. 10,045,812.

(60) Provisional application No. 62/035,751, filed on Aug. 11, 2014, provisional application No. 62/035,764, filed on Aug. 11, 2014.

(51) Int. Cl.
A61B 18/14 (2006.01)
A61B 17/26 (2006.01)
A61B 18/00 (2006.01)
A61B 17/29 (2006.01)

(52) U.S. Cl.
CPC .......... *A61B 18/1445* (2013.01); *A61B 17/26* (2013.01); *A61B 18/1442* (2013.01);
(Continued)

(58) Field of Classification Search
CPC . A61B 18/1445; A61B 17/26; A61B 18/1442; A61B 18/1447; A61B 2017/2926; A61B 2018/00327; A61B 2017/2944
See application file for complete search history.

(56) References Cited

U.S. PATENT DOCUMENTS

D263,020 S    2/1982  Rau, III
D295,893 S    5/1988  Sharkany et al.
(Continued)

FOREIGN PATENT DOCUMENTS

DE    2415263 A1    10/1975
DE    02514501 A1   10/1976
(Continued)

OTHER PUBLICATIONS

US. Appl. No. 09/387,883, filed Sep. 1, 1999.
(Continued)

*Primary Examiner* — Linda C Dvorak
*Assistant Examiner* — Ryan T Clark

(57) ABSTRACT

A method of surgery includes grasping tissue between tissue-treating plates of first and second jaw members. One or both of the jaw members includes a bifurcated body having first and second jaw components. Each jaw component includes a tissue-treating plate portion disposed thereon. The tissue-treating plate portions cooperate to define the tissue-treating plate of the jaw member. The method further includes energizing the tissue-treating plates of the first and second jaw members for conducting energy through grasped tissue to treat grasped tissue and separating grasped and treated tissue by rotating at least one of the first and second jaw components of the at least one jaw member relative to the other from an aligned orientation, wherein the tissue-treating plate portions are substantially co-planar relative to one another, to an angled orientation, wherein the tissue-treating plate portions are angled relative to one another.

8 Claims, 7 Drawing Sheets

(52) U.S. Cl.
CPC ... *A61B 18/1447* (2013.01); *A61B 2017/2926* (2013.01); *A61B 2017/2944* (2013.01); *A61B 2018/00327* (2013.01); *A61B 2018/1457* (2013.01)

(56) References Cited

U.S. PATENT DOCUMENTS

| | | | |
|---|---|---|---|
| D295,894 S | 5/1988 | Sharkany et al. | |
| 5,190,541 A | 3/1993 | Abele et al. | |
| 5,254,129 A | 10/1993 | Alexander | |
| 5,320,636 A * | 6/1994 | Slater | A61B 17/320016 606/205 |
| 5,324,289 A | 6/1994 | Eggers | |
| D348,930 S | 7/1994 | Olson | |
| 5,352,222 A | 10/1994 | Rydell | |
| 5,456,684 A | 10/1995 | Schmidt et al. | |
| 5,573,535 A | 11/1996 | Viklund | |
| 5,613,499 A | 3/1997 | Palmer et al. | |
| 5,637,111 A | 6/1997 | Sutcu et al. | |
| D384,413 S | 9/1997 | Zlock et al. | |
| 5,700,261 A | 12/1997 | Brinkerhoff | |
| 5,779,701 A | 7/1998 | McBrayer et al. | |
| 5,827,281 A | 10/1998 | Levin | |
| 5,964,758 A | 10/1999 | Dresden | |
| 5,984,938 A | 11/1999 | Yoon | |
| D424,694 S | 5/2000 | Tetzlaff et al. | |
| D425,201 S | 5/2000 | Tetzlaff et al. | |
| 6,179,837 B1 | 1/2001 | Hooven | |
| D449,886 S | 10/2001 | Tetzlaff et al. | |
| 6,350,264 B1 | 2/2002 | Hooven | |
| 6,358,268 B1 | 3/2002 | Hunt et al. | |
| 6,361,534 B1 | 3/2002 | Chen et al. | |
| D457,958 S | 5/2002 | Dycus et al. | |
| D457,959 S | 5/2002 | Tetzlaff et al. | |
| 6,425,896 B1 | 7/2002 | Baltschun et al. | |
| 6,464,701 B1 | 10/2002 | Hooven et al. | |
| 6,520,960 B2 | 2/2003 | Blocher et al. | |
| D493,888 S | 8/2004 | Reschke | |
| 6,773,434 B2 | 8/2004 | Ciarrocca | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,270,660 B2 | 9/2007 | Ryan | |
| 7,329,257 B2 | 2/2008 | Kanehira et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,470,276 B2 | 12/2008 | Tu | |
| 7,621,910 B2 | 11/2009 | Sugi | |
| 7,686,804 B2 | 3/2010 | Johnson et al. | |
| 7,717,914 B2 | 5/2010 | Kimura | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 8,035,129 B2 | 10/2011 | Ramaswamy et al. | |
| 8,112,871 B2 | 2/2012 | Brandt et al. | |
| 8,133,254 B2 | 3/2012 | Dumbauld et al. | |
| 8,162,965 B2 | 4/2012 | Reschke et al. | |
| 8,187,273 B2 | 5/2012 | Kerr et al. | |
| 8,192,433 B2 | 6/2012 | Johnson et al. | |
| 8,226,650 B2 | 7/2012 | Kerr | |
| 8,241,282 B2 | 8/2012 | Unger et al. | |
| 8,251,994 B2 | 8/2012 | McKenna et al. | |
| 8,252,626 B2 | 8/2012 | Cho et al. | |
| 8,266,783 B2 | 9/2012 | Brandt et al. | |
| 8,277,446 B2 | 10/2012 | Heard | |
| 8,287,536 B2 | 10/2012 | Mueller et al. | |
| 8,292,067 B2 | 10/2012 | Chowaniec et al. | |
| 8,292,886 B2 | 10/2012 | Kerr et al. | |
| 8,323,310 B2 | 12/2012 | Kingsley | |
| 8,343,150 B2 | 1/2013 | Artale | |
| 8,343,151 B2 | 1/2013 | Siebrecht et al. | |
| 8,357,159 B2 | 1/2013 | Romero | |
| 8,388,647 B2 | 3/2013 | Nau, Jr. et al. | |
| 8,409,246 B2 | 4/2013 | Kerr et al. | |
| 8,409,247 B2 | 4/2013 | Garrison et al. | |
| 8,425,511 B2 | 4/2013 | Olson | |
| 8,430,876 B2 | 4/2013 | Kappus et al. | |
| 8,430,877 B2 | 4/2013 | Kerr et al. | |
| 8,439,911 B2 | 5/2013 | Mueller | |
| 8,439,913 B2 | 5/2013 | Horner et al. | |
| 8,469,991 B2 | 6/2013 | Kerr | |
| 8,469,992 B2 | 6/2013 | Roy et al. | |
| 8,480,671 B2 | 7/2013 | Mueller | |
| 8,491,624 B2 | 7/2013 | Kerr et al. | |
| 8,491,625 B2 | 7/2013 | Horner | |
| 8,491,626 B2 | 7/2013 | Roy et al. | |
| 8,512,336 B2 | 8/2013 | Couture | |
| 8,512,371 B2 | 8/2013 | Kerr et al. | |
| 8,540,749 B2 | 9/2013 | Garrison et al. | |
| 8,556,929 B2 | 10/2013 | Harper et al. | |
| 8,568,397 B2 | 10/2013 | Horner et al. | |
| 8,568,412 B2 | 10/2013 | Brandt et al. | |
| 8,585,736 B2 | 11/2013 | Horner et al. | |
| 8,597,295 B2 | 12/2013 | Kerr | |
| 8,623,018 B2 | 1/2014 | Horner et al. | |
| 8,647,343 B2 | 2/2014 | Chojin et al. | |
| 8,668,689 B2 | 3/2014 | Dumbauld et al. | |
| 8,672,939 B2 | 3/2014 | Garrison | |
| 8,679,114 B2 | 3/2014 | Chapman et al. | |
| 8,679,115 B2 | 3/2014 | Reschke | |
| 8,740,898 B2 | 6/2014 | Chojin et al. | |
| 8,777,945 B2 | 7/2014 | Floume et al. | |
| 8,808,288 B2 | 8/2014 | Reschke | |
| 8,961,504 B2 | 2/2015 | Hoarau et al. | |
| 8,968,358 B2 | 3/2015 | Reschke | |
| 8,968,359 B2 | 3/2015 | Kerr et al. | |
| 9,024,237 B2 | 5/2015 | Bonn | |
| 9,060,798 B2 | 6/2015 | Harper et al. | |
| 2003/0018332 A1 | 1/2003 | Schmaltz et al. | |
| 2003/0065358 A1 | 4/2003 | Frecker et al. | |
| 2003/0171747 A1 | 9/2003 | Kanehira et al. | |
| 2008/0004616 A1 | 1/2008 | Patrick | |
| 2009/0187188 A1 | 7/2009 | Guerra et al. | |
| 2009/0209991 A1 | 8/2009 | Hinchliffe et al. | |
| 2010/0229644 A1 | 9/2010 | Curtis | |
| 2010/0249769 A1 | 9/2010 | Nau, Jr. et al. | |
| 2010/0280511 A1 | 11/2010 | Rachlin et al. | |
| 2011/0034918 A1 | 2/2011 | Reschke | |
| 2011/0054468 A1 | 3/2011 | Dycus | |
| 2011/0054471 A1 | 3/2011 | Gerhardt et al. | |
| 2011/0060335 A1 | 3/2011 | Harper et al. | |
| 2011/0071523 A1 | 3/2011 | Dickhans | |
| 2011/0193608 A1 | 8/2011 | Krapohl | |
| 2011/0270245 A1 | 11/2011 | Horner et al. | |
| 2011/0270251 A1 | 11/2011 | Horner et al. | |
| 2011/0276049 A1 | 11/2011 | Gerhardt | |
| 2011/0295313 A1 | 12/2011 | Kerr | |
| 2011/0319886 A1 | 12/2011 | Chojin et al. | |
| 2014/0135804 A1 * | 5/2014 | Weisenburgh, II | A61B 17/320092 606/169 |
| 2014/0276786 A1 * | 9/2014 | Batchelor | A61B 18/1442 606/41 |
| 2016/0045770 A1 * | 2/2016 | Yamada | A61B 17/320068 601/2 |

FOREIGN PATENT DOCUMENTS

| | | |
|---|---|---|
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |

(56) References Cited

FOREIGN PATENT DOCUMENTS

| | | |
|---|---|---|
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 10045375 C2 | 10/2002 |
| DE | 202007009317 U1 | 10/2007 |
| DE | 102004026179 B4 | 1/2009 |
| EP | 1159926 A3 | 3/2003 |
| EP | 1330991 A1 | 7/2003 |
| EP | 0913126 B1 | 10/2004 |
| JP | 61501068 | 9/1984 |
| JP | 6502328 | 3/1992 |
| JP | 55106 | 1/1993 |
| JP | 0540112 | 2/1993 |
| JP | 06343644 A | 12/1994 |
| JP | 07265328 A | 10/1995 |
| JP | H0856955 | 5/1996 |
| JP | 08252263 A | 10/1996 |
| JP | H0910223 A | 1/1997 |
| JP | 11070124 A | 3/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 0036986 A1 | 6/2000 |
| WO | 0059392 A1 | 10/2000 |
| WO | 0154604 A1 | 8/2001 |
| WO | 0166025 | 9/2001 |
| WO | 2005110264 A3 | 4/2006 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleytab LigaSure Device in the Hemostasis of Small, Medium and Large-Sized Arteries" Carolinas Laparoscopic and Advanced Surgery Program, Carolinas Laparoscopic and AdvancedSurgery Program, Carolinas Medical Center, Charlotte, NC.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.

(56) References Cited

OTHER PUBLICATIONS

Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Bergdahl et al. "Studies on Coagulation and the Development of an Automatic Computerized Bipolar Coagulator" J. Neurosurg, vol. 75, Jul. 1991, pp. 148-151.

\* cited by examiner

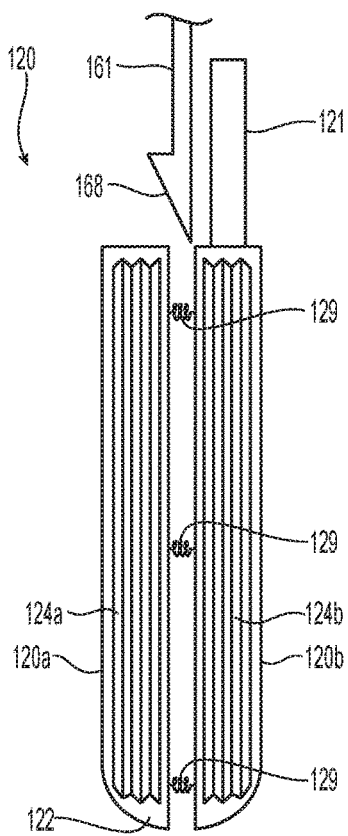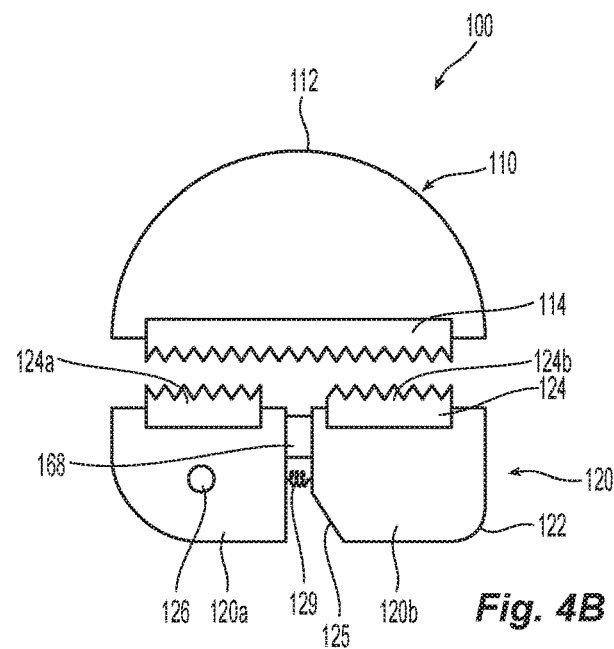
Fig. 4A
Fig. 4B
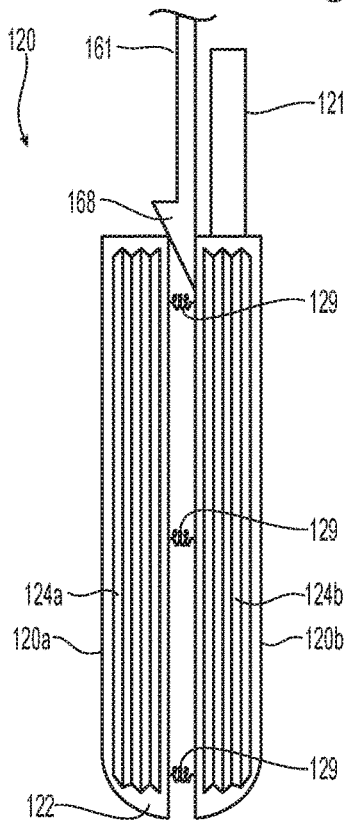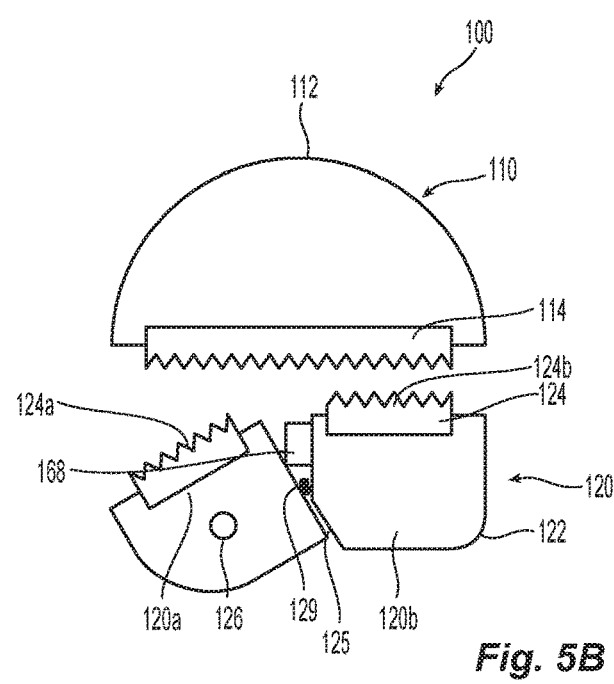
Fig. 5A
Fig. 5B

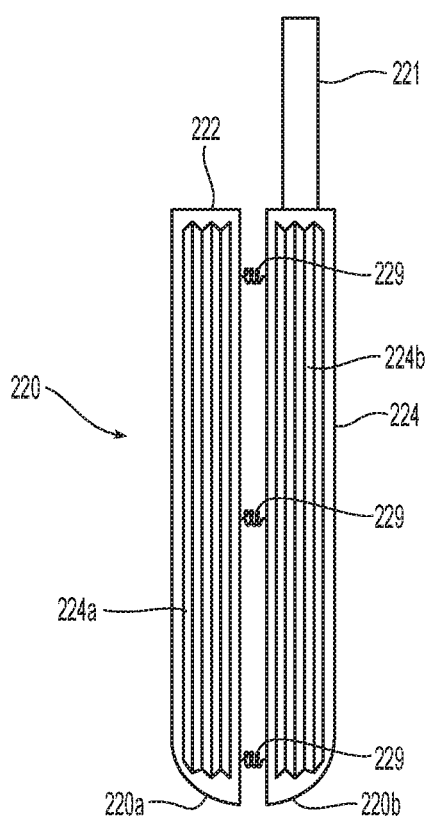
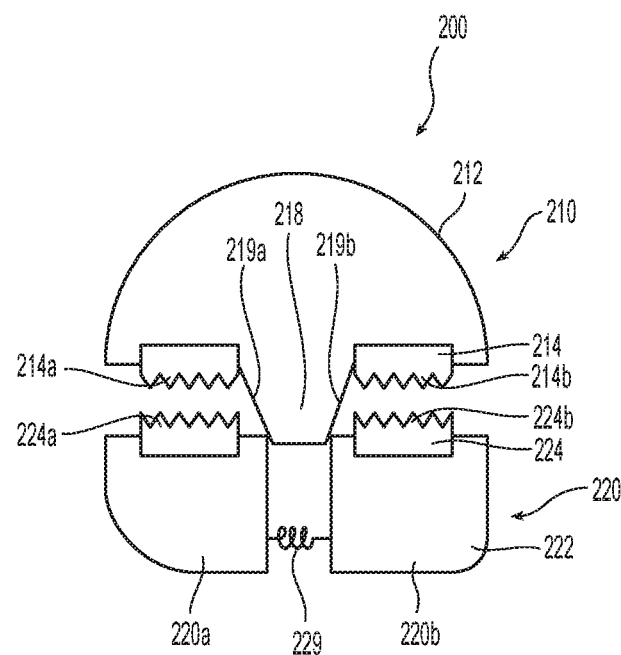
Fig. 6A
Fig. 6B
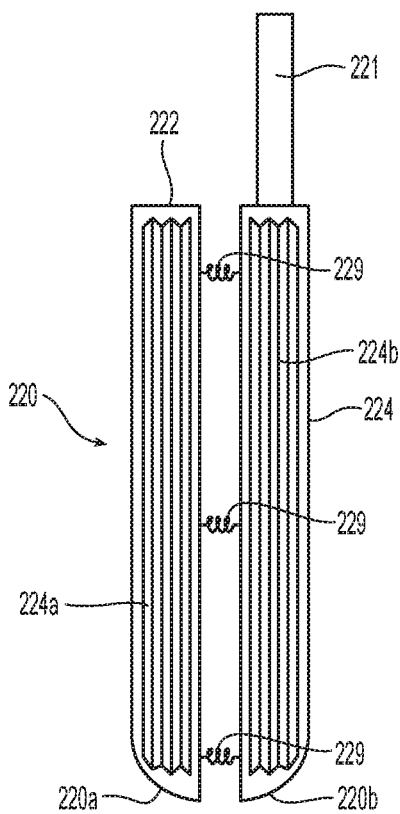
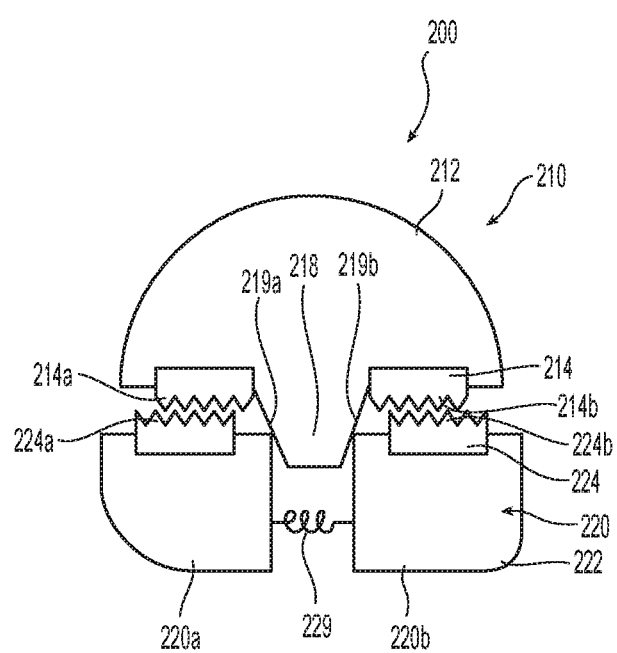
Fig. 7A
Fig. 7B

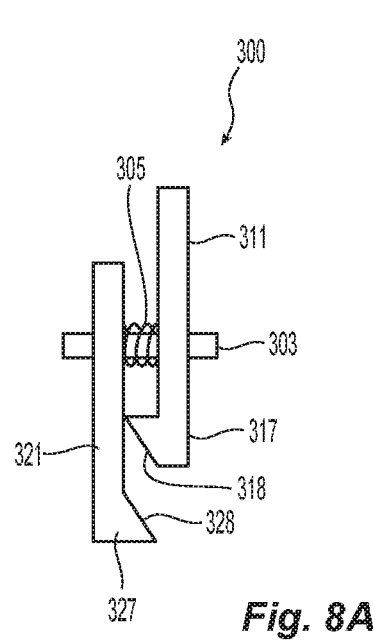
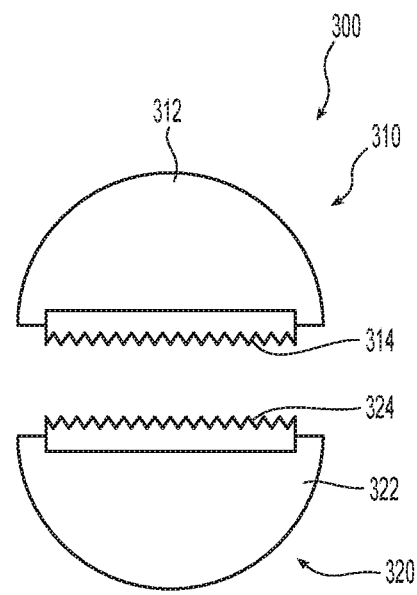
Fig. 8A
Fig. 8B
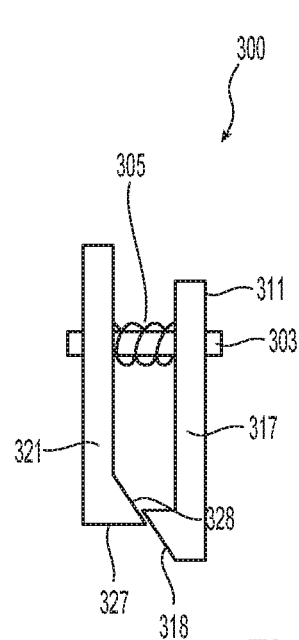
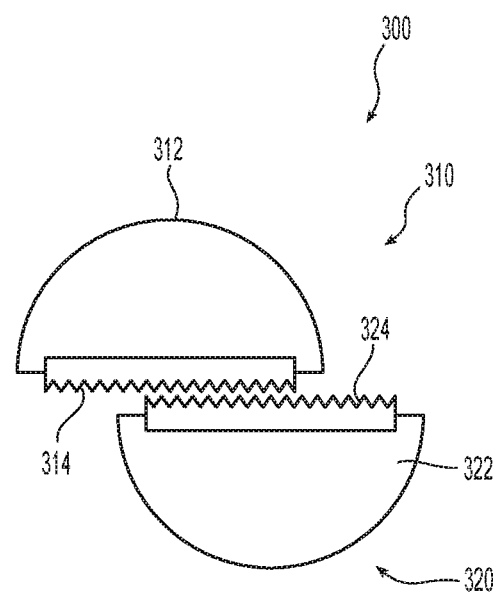
Fig. 9A
Fig. 9B

SURGICAL INSTRUMENTS AND METHODS FOR PERFORMING TONSILLECTOMY AND ADENOIDECTOMY PROCEDURES

CROSS-REFERENCE TO RELATED APPLICATIONS

This application is a continuation application of U.S. patent application Ser. No. 14/738,201, filed on Jun. 12, 2015, which claims the benefit of, and priority to, U.S. Provisional Patent Application Nos. 62/035,751 and 62/035,764, both of which were filed on Aug. 11, 2014. This application is related to U.S. patent application Ser. No. 14/738,107, filed on Jun. 12, 2015, now abandoned. The entire contents of each of the above applications are hereby incorporated herein by reference.

BACKGROUND

Technical Field

The present disclosure relates to surgical instruments and methods and, more particularly, to surgical instruments and methods for performing tonsillectomy and/or adenoidectomy procedures.

Background of Related Art

The tonsils and adenoids are part of the lymphatic system and are generally located in the back of the throat. These parts of the lymphatic system are generally used for sampling bacteria and viruses entering the body and activating the immune system when warranted to produce antibodies to fight oncoming infections. More particularly, the tonsils and adenoids break down the bacteria or virus and send pieces of the bacteria or virus to the immune system to produce antibodies for fighting off infections.

Inflammation of the tonsils and adenoids (e.g., tonsillitis) impedes the ability of the tonsils and adenoids to destroy the bacteria resulting in a bacterial infection. In many instances, the bacteria remain even after treatment and serve as a reservoir for repeated infections (e.g., tonsillitis or ear infections).

A tonsillectomy and/or adenoidectomy may be performed when infections persist and antibiotic treatments fail. Persistent infection typically leads to enlarged tonsil tissue which may need to be removed since in many cases the enlarged tissue causes airway obstruction leading to various sleep disorders such as snoring or, in some cases, sleep apnea. Some individuals are also born with larger tonsils that are more prone to cause obstruction. An adenoidectomy may also be required to remove adenoid tissue when ear pain persists, or when nose breathing or function of the Eustachian tube is impaired. Often times, tonsillectomy and adenoidectomy procedures are performed at the same time.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A method of surgery provided in accordance with aspects of the present disclosure utilizes an end effector assembly including first and second jaw members. At least one of the jaw members includes a bifurcated body having first and second jaw components. Each of the jaw components includes a tissue-treating plate portion disposed thereon. The tissue-treating plate portions cooperate to define the tissue-treating plate of the jaw member. The method includes grasping tissue between the tissue-treating plates of the first and second jaw members, energizing the tissue-treating plates of the first and second jaw members for conducting energy through grasped tissue to treat grasped tissue, and separating grasped and treated tissue by rotating at least one of the first and second jaw components of the at least one jaw member relative to the other from an aligned orientation, wherein the tissue-treating plate portions are substantially co-planar relative to one another, to an angled orientation, wherein the tissue-treating plate portions are angled relative to one another.

In an aspect of the present disclosure, grasping tissue includes compressing a movable handle relative to a fixed handle to pivot the first and second jaw members from a spaced-apart position to an approximated position.

In another aspect of the present disclosure, separating grasped and treated tissue includes actuating a trigger to translate an actuation member from a first position to a second position to rotate the at least one of the first and second jaw components from the aligned orientation to the angled orientation.

Another method of surgery provided in accordance with aspects of the present disclosure includes utilizing and end effector assembly including first and second jaw members each including first and second spaced-apart tissue-treating plate portions. At least one of the jaw members includes a bifurcated body having a first jaw component including the first tissue-treating plate portion thereof and a second jaw component including the second tissue-treating plate portion thereof. The method includes grasping tissue between the first tissue-treating plate portions of the jaw members and between the second tissue-treating plate portions of the jaw members by moving the first and second jaw members from a spaced-apart position to a first approximated position, energizing the tissue-treating plate portions of the first and second jaw members for conducting energy through grasped tissue to treat grasped tissue, and separating grasped and treated tissue by moving the first and second jaw components of the at least one jaw member laterally apart from one another.

In an aspect of the present disclosure, separating grasped and treated tissue includes moving the first and second jaw members from the first approximated position to a second approximated position. In such aspects, moving the first and second jaw members from the first approximated position to the second approximated position urges the first and second jaw components of the at least one jaw member laterally apart from one another.

In another aspect of the present disclosure, grasping tissue includes compressing a movable handle relative to a fixed handle from an initial position to a first compressed position to move the jaw members from the spaced-apart position to the first approximated position and separating grasped and treated tissue includes compressing the movable handle from the first compressed position to a second compressed position to move the jaw members from the first approximated position to the second approximated position.

In yet another aspect of the present disclosure, the first jaw member includes an insulative member disposed between the tissue-treating plate portions thereof and the second jaw member includes the bifurcated body having the first jaw component and the second jaw component. In such aspects, moving the first and second jaw members from the first approximated position to the second approximated position urges the insulative member at least partially between the first and second jaw components to urge the first and second jaw components laterally apart from one another.

In still another aspect of the present disclosure, each of the jaw members includes a bifurcated body having a first jaw component including the first tissue-treating plate portion thereof and a second jaw component including the second tissue-treating plate portion thereof. In such aspects, separating grasped and treated tissue includes moving the first jaw components of the first and second jaw members and the second jaw components of the first and second jaw components laterally apart from one another.

Another method of surgery provided in accordance with the present disclosure includes grasping tissue between tissue-treating plates of first and second jaw members by moving the first and second jaw members from a spaced-apart position to a first approximated position, energizing the tissue-treating plates of the first and second jaw members for conducting energy through grasped tissue to treat grasped tissue, and separating grasped and treated tissue by moving the first and second jaw members from the first approximated position to a second approximated position. Moving the first and second jaw members from the first approximated position to the second approximated position laterally shifts the jaw members relative to one another from an aligned orientation, wherein the tissue-treating plates are aligned with one another, to an offset orientation, wherein the tissue-treating plates are offset relative to one another.

In aspects, grasping tissue includes compressing a movable handle relative to a fixed handle from an initial position to a first compressed position to move the jaw members from the spaced-apart position to the first approximated position and separating grasped and treated tissue includes compressing the movable handle from the first compressed position to a second compressed position to move the jaw members from the first approximated position to the second approximated position.

BRIEF DESCRIPTION OF THE DRAWINGS

Various aspects and features of the present disclosure are described herein with reference to the drawings wherein:

FIG. 4A is a top view of one of the jaw members of the end effector assembly of FIG. 3B and the actuation assembly of FIG. 3A-3B, disposed in an un-actuated condition;

FIG. 4B is a transverse, cross-sectional view of the end effector assembly of FIG. 3B and the actuation assembly of FIG. 3A-3B, disposed in the un-actuated condition;

FIG. 5A is a top view of jaw member of FIG. 3B and the actuation assembly of FIG. 3A-3B, disposed in an actuated condition;

FIG. 5B is a transverse, cross-sectional view of the end effector assembly of FIG. 3B and the actuation assembly of FIG. 3A-3B, disposed in the actuated condition;

FIG. 6A is a top view of one of the jaw members of another end effector assembly provided in accordance with the present disclosure, disposed in an un-actuated condition;

FIG. 6B is a transverse, cross-sectional view of the end effector assembly of FIG. 6A, disposed in the un-actuated condition;

FIG. 7A is a top view of the jaw member of FIG. 6A, disposed in an actuated condition;

FIG. 7B is a transverse, cross-sectional view of the end effector assembly of FIG. 7A, disposed in the actuated condition;

FIG. 8A is a transverse, cross-sectional view of proximal flanges of the jaw members of another end effector assembly provided in accordance with the present disclosure, disposed in an un-actuated condition;

FIG. 8B is a transverse, cross-sectional view of the jaw bodies of the jaw members of the end effector assembly of FIG. 8A, disposed in the un-actuated condition;

FIG. 9A is a is a transverse, cross-sectional view of the proximal flanges of the jaw members of the end effector assembly of FIG. 8A, disposed in an actuated condition;

FIG. 9B is a transverse, cross-sectional view of the jaw bodies of the jaw members of the end effector assembly of FIG. 8A, disposed in the actuated condition;

DETAILED DESCRIPTION

Figure 1:
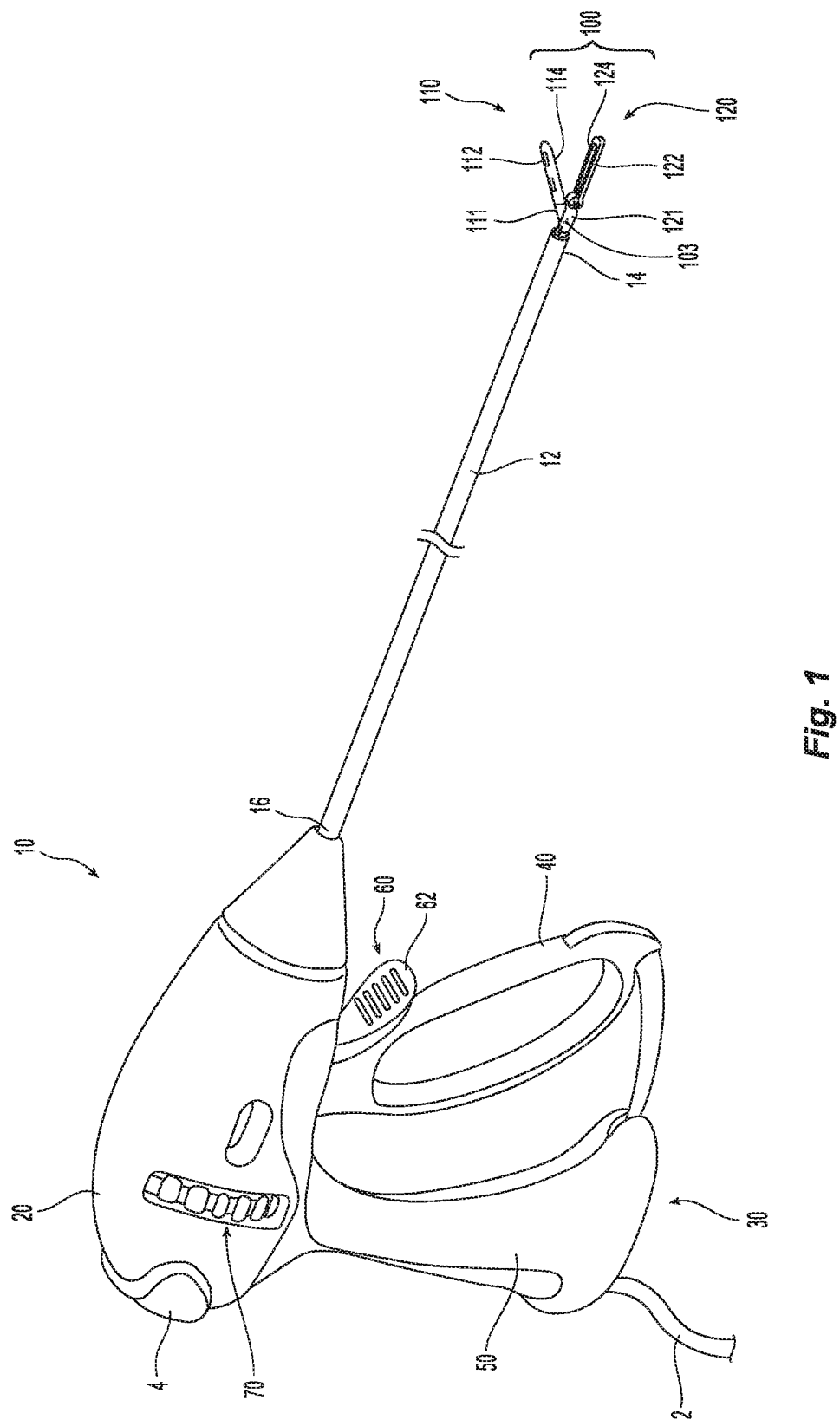
FIG. 1 is a front, side, perspective view of an endoscopic surgical forceps configured for use in accordance with the present disclosure.
Figure 2:
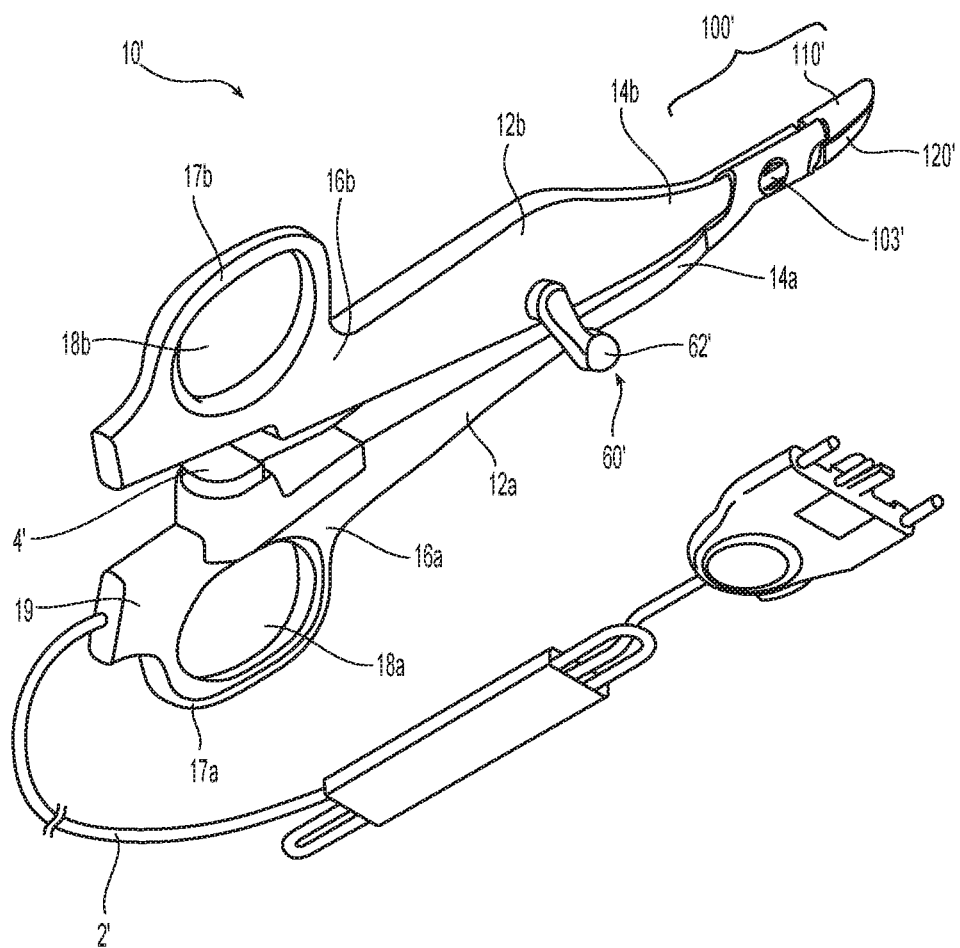
FIG. 2 is a front, side, perspective view of an open surgical forceps configured for use in accordance with the present disclosure.

Turning to FIGS. 1 and 2, FIG. 1 depicts a handheld, shaft-based surgical forceps 10 and FIG. 2 depicts a hemostat-style forceps 10'. For the purposes herein, either forceps 10, forceps 10', or any other suitable surgical instrument may be utilized in accordance with the present disclosure. Obviously, different electrical and mechanical connections and considerations apply to each particular type of instrument; however, the aspects and features of the present disclosure remain generally consistent regardless of the particular instrument used.

Referring to FIG. 1, forceps 10 generally includes a housing 20, a handle assembly 30, an actuation assembly 60, a rotating assembly 70, an activation switch 4, and an end effector assembly 100. Forceps 10 further includes a shaft 12 having a distal end 14 configured to mechanically engage end effector assembly 100 and a proximal end 16 that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating plates 114, 124 (FIG. 3B) of jaw members 110, 120, respectively. Activation switch 4 is coupled to tissue-treating plates 114, 124 (FIG. 3B) of jaw members 110, 120, respectively, and the source of energy for selectively activating the supply of energy to jaw members 110, 120 for treating, e.g., cauterizing, coagulating/desiccating, and/or sealing, tissue.

Figure 3A:
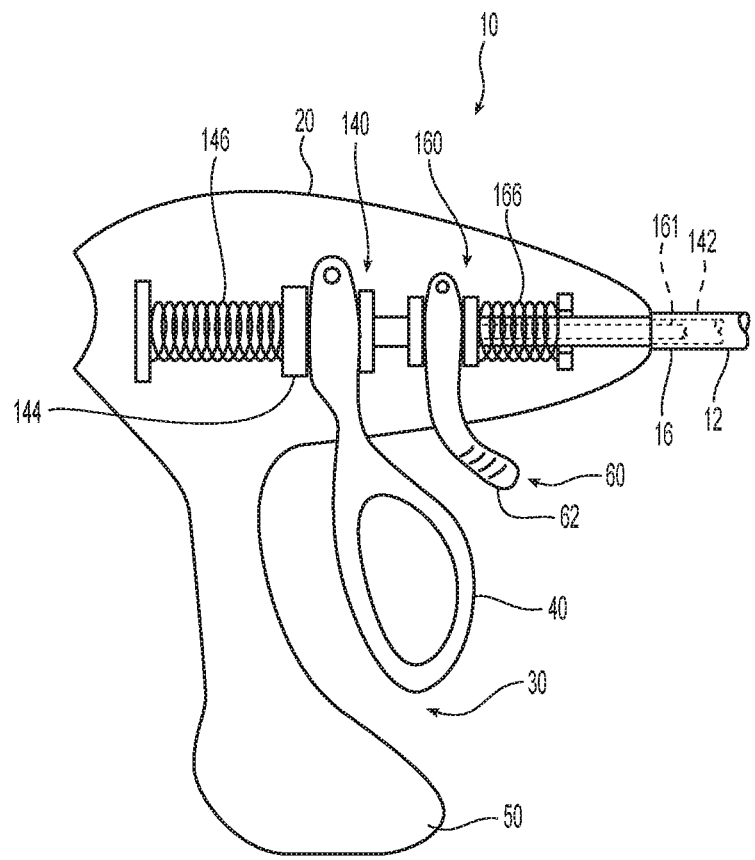
FIG. 3A is a side, cut-away view of the proximal portion of the surgical forceps of FIG. 1, wherein a portion of the housing and some of the internal components thereof have been removed to unobstructively illustrate the handle, actuation, and drive assemblies of the forceps.
Figure 3B:
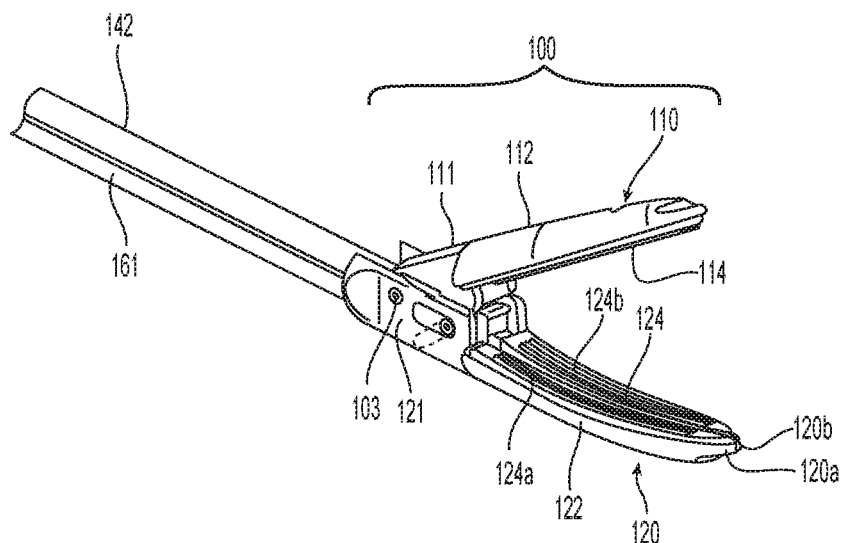
FIG. 3B is a perspective, cut-away view of the distal portion of the surgical forceps of FIG. 1, wherein the shaft has been removed to illustrate the drive bar, actuation assembly, and end effector assembly of the forceps.

With additional reference to FIGS. 3A and 3B, handle assembly 30 includes fixed handle 50 and a movable handle 40. Fixed handle 50 is integrally associated with housing 20 and handle 40 is movable relative to fixed handle 50. Movable handle 40 of handle assembly 30 is operably coupled to a drive assembly 140 that, together, mechanically cooperate to impart movement of one or both of jaw members 110, 120 about a pivot 103 between a spaced-apart position and an approximated position to grasp tissue between jaw members 110, 120. In particular, movable handle 40 is coupled to drive bar 142 via a drive mandrel 144 such that movement of movable handle 40 relative to housing 20 effects longitudinal translation of drive bar 142 through housing 20 and shaft 12. The distal end of drive bar 142 is coupled to one or both jaw members 110, 120 such that longitudinal translation of drive bar 142 relative to end effector assembly 100 pivots one or both of jaw members 110, 120 relative to one another. As shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. Further, a biasing member 146 may be disposed within housing 20 and positioned to bias drive bar 142 distally, thereby biasing jaw members 110, 120 towards the spaced-apart position. However, other configurations are also contemplated.

Actuation assembly 60 includes a trigger 62 coupled to housing 20 and movable relative thereto between an un-actuated position and an actuated position. More specifically, trigger 62 is operably coupled to an actuation bar 161 (e.g., similarly as with the coupling of movable handle 40 to drive bar 142) such that movement of trigger 62 relative to housing 20 effects longitudinal translation of actuation bar 161 through housing 20 and shaft 12. The distal end of actuation bar 161 is coupled to one or both jaw members 110, 120 such that longitudinal translation of actuation bar 161 effects transitioning of end effector assembly 100 between the un-actuated condition (FIGS. 4A and 4B) and the actuated condition (FIGS. 5A and 5B). Trigger 62, as shown in FIG. 1, is initially disposed in the un-actuated position and, correspondingly, end effector assembly 100 is disposed in the un-actuated condition (FIGS. 4A and 4B). Trigger 62 is selectively actuatable from this un-actuated position to an actuated position corresponding to the actuated condition of end effector assembly 100 (FIGS. 5A and 5B). Further, a biasing member 166 may be disposed within housing 20 and positioned to bias actuation bar 161 proximally, thereby biasing end effector assembly 100 towards the un-actuated condition and trigger 62 towards the un-actuated position. The operable distal components of actuation assembly 60 and the functions thereof are described in greater detail below.

Referring to FIG. 2, forceps 10' is shown including two elongated shaft members 12a, 12b, each having a proximal end 16a, 16b, and a distal end 14a, 14b, respectively. Forceps 10' is configured for use with an end effector assembly 100' similar to end effector assembly 100 (FIGS. 1 and 3B). More specifically, end effector assembly 100' includes first and second jaw members 110', 120' attached to respective distal ends 14a, 14b of shaft members 12a, 12b. Jaw members 110', 120' are pivotably connected about a pivot 103'. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of the shaft members 12a, 12b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 12a, 12b of forceps 10', e.g., shaft member 12a, includes a proximal shaft connector 19 configured to connect the forceps 10' to a source of energy (not shown), e.g., a generator. Proximal shaft connector 19 secures a cable 2' to forceps 10' such that the user may selectively supply energy to jaw members 110', 120' for treating tissue and for energy-based tissue cutting. More specifically, an activation switch 4' is provided for supplying energy to jaw members 110', 120' to treat tissue upon sufficient approximation of shaft members 12a, 12b, e.g., upon activation of activation switch 4' via shaft member 12b.

Forceps 10' further includes an actuation assembly 60' including a trigger 62' coupled to one of the shaft members, e.g., shaft member 12b, and movable relative thereto between an un-actuated position and an actuated position for transitioning end effector assembly 100' between an un-actuated condition and an actuated condition, similarly as with end effector assembly 100 (FIG. 3B).

With reference to FIG. 3B, end effector assembly 100 of forceps 10 (FIG. 1) is shown, although end effector assembly 100 may similarly be used in conjunction with forceps 10' (FIG. 2), or any other suitable surgical instrument. For purposes of simplicity, end effector assembly 100 is described herein as configured for use with forceps 10 (FIG. 1). Further, end effector assembly 100 is initially generally described below with reference to FIG. 3B, followed by a more detailed description of the particular features and function thereof with reference to FIGS. 4A-5B. End effector assembly 100, and the various other configurations of end effector assemblies detailed below with respect to FIGS. 6A-10B, are suitable for use in performing tonsillectomy and/or adenoidectomy procedures, although such end effector assemblies may equally be applicable for use in other surgical procedures. Each of the various configurations detailed below with respect to FIGS. 6A-10B may incorporate the general features of end effector assembly 100 and may likewise be used with forceps 10 (FIG. 1), forceps 10' (FIG. 2), or any other suitable surgical instrument. That is, the general features detailed with respect to end effector assembly 100 (FIG. 3B), are also applicable to the end effector assemblies of FIGS. 6A-10, except where specifically contradicted.

Each jaw member 110, 120 of end effector assembly 100 includes a jaw frame having a proximal flange portion 111, 121, an outer insulative jaw housing 112, 122 disposed about the distal portion (not explicitly shown) of each jaw frame, and a tissue-treating plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw frames are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-treating plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 (FIG. 1) and the source of energy (not shown), e.g., via the wires (not shown) extending from cable 2 (FIG. 1) through forceps 10 (FIG. 1), such that energy may be selectively supplied to tissue-treating plate 114 and/or tissue-treating plate 124 and conducted therebetween and through tissue disposed between jaw members 110, 120 to treat tissue. Tissue-treating plates 114, 124 may define serrated configurations to facilitate grasping and cutting of tissue, as detailed below.

With additional reference to FIGS. 4A-5B, one of the jaw members of end effector assembly 100, e.g., jaw member 120, defines a bifurcated configuration including first and second jaw components 120a, 120b. First and second jaw components 120a, 120b of jaw member 120 extend longitudinally in side-by-side relation relative to one another and each includes a tissue-treating plate portion 124a, 124b that together form tissue-treating plate 124. Although shown as substantially equal, it is envisioned that jaw components 120a, 120b may define any suitable equal or unequal widths.

One of the jaw components of jaw member 120, e.g., jaw component 120a, is rotatably coupled to proximal flange portion 121 of jaw member 120 via a rod 126, although it is also contemplated that both jaw components 120a, 120b be rotatable relative to proximal flange portion 121. Rod 126 extends longitudinally such that jaw component 120a is rotatable between an aligned orientation, corresponding to the un-actuated condition of end effector assembly 100, wherein tissue-treating plate portion 124a and tissue-treating plate portion 124b are substantially coplanar relative to one another (FIGS. 4A and 4B), and an angled orientation, corresponding to the actuated condition of end effector assembly 100, wherein tissue-treating plate portion 124a is angled with respect to tissue-treating plate portion 124b (FIGS. 5A and 5B). Further, one of the jaw components, e.g., jaw component 120b, may define a cut-out 125 to permit rotation of jaw component 120a relative thereto.

Actuator drive bar 161 of actuator assembly 60 (FIG. 3A) includes an actuator member 168 disposed at the distal end thereof that is configured for insertion between jaw components 120a, 120b to rotate jaw component 120b relative to jaw component 120a, thereby rotating tissue-treating plate portion 124a relative to tissue-treating plate portion 124b from the aligned orientation to the angled orientation. More specifically, actuator member 168 defines a wedge-like configuration and is configured for insertion between jaw components 120a, 120b at a position offset, e.g., above or below, relative to rod 126. As such, insertion of the wedge-like actuator member 168 jaw components 120a, 120b urges jaw component 120a and tissue-treating plate portion 124a thereof to rotate towards the angled orientation. Trigger 62 of actuator assembly 60 (FIG. 3A), as noted above, is selectively actuatable to advance actuator drive bar 161 and, thus, actuator member 168 between jaw components 120a, 120b to transition end effector assembly 100 to the actuated condition. One or more biasing members 129 may be disposed between jaw components 120a, 120b at a position offset relative to rod 126, on an opposite side of rod 126 as compared to actuator member 168 to bias jaw components 120a, 120b towards the aligned orientation, corresponding to the un-actuated condition of end effector assembly 100.

In use, with end effector assembly 100 disposed in the un-actuated condition (FIGS. 4A and 4B) and jaw members 110, 120 disposed in the spaced-apart position, end effector assembly 100 is manipulated into position such that tissue to be treated and cut is disposed between jaw members 110, 120. With respect to tonsillectomy procedures, for example, end effector assembly 100 is positioned between the cavity wall tissue (or other tissue to remain) and the tonsil tissue (or other tissue to be removed). Once the desired position has been achieved, jaw members 110, 120 are moved to the approximated position, e.g., via moving movable handle 40 (FIG. 3A) to the depressed condition, to grasp tissue between tissue-treating plate 114 and tissue-treating plates 124a, 124b. Thereafter, tissue-treating plate 114 may be energized to a first electrical potential and tissue-treating plate portions 124a, 124b to a second, different electrical potential for conducting energy between plate 114 and plate portions 124a, 124b and through tissue grasped therebetween to treat tissue.

Once tissue has been treated the tissue to be removed, e.g., the tonsil tissue, is separated from the tissue to remain, e.g., the wall tissue. In order to separate the tissue, while maintaining jaw members 110, 120 in the approximated position grasping the previously treated tissue between the serrated tissue-treating plate 114 and plate portions 124a, 124b, trigger 62 (FIG. 3A) is moved from the un-actuated position to the actuated position. Actuation of trigger 62 (FIG. 3A) advances actuation drive rod 161 and actuation member 168 distally such that actuation member 168 is inserted between jaw components 120a, 120b to urge jaw component 120a to rotate relative to jaw component 120b from the aligned orientation, e.g., the un-actuated condition of end effector assembly 100, to the angled orientation, e.g., the actuated condition of end effector assembly 100. As tissue-treating plate portion 124a is rotated relative to tissue-treating plate portion 124b and tissue-treating plate 114, the previously treated tissue grasped between jaw members 110, 120, which is substantially held in position via the serrated tissue-treating plate 114 and plate portions 124a, 124b, is cut in a dynamic shearing and/or ripping fashion, ultimately separating the tonsil tissue to be removed from the wall tissue to remain. The separated tonsil tissue may then be removed using end effector assembly 100, another grasping instrument, a suction device, or via other suitable method.

Turning to FIGS. 6A-7B, another embodiment of an end effector assembly is shown generally identified by reference numeral 200. End effector assembly 200 may be configured for use with forceps 10 (FIG. 1), forceps 10' (FIG. 2), or any other suitable surgical instrument, except that actuation assembly 60, 60' (FIGS. 1 and 2, respectively), need not be provided. Rather, as detailed below, end effector assembly 200 is configured for treating and cutting tissue by moving jaw members 210, 220 from a spaced-apart position to a first approximated position to grasp and treat tissue, and further to a second approximated position to cut tissue. With additional reference to FIG. 1 momentarily, this may be accomplished, for example, via moving movable handle 40 of forceps 10 from the initial position to a first compressed position corresponding to the first approximated position of jaw members 210, 220, and to then further to a second approximated position of jaw members 210, 220.

Each jaw member 210, 220 of end effector assembly 200 includes a jaw frame having a proximal flange portion 221 (although not shown, the proximal flange portion of jaw member 210 is similar proximal flange portion 221 of jaw member 220), an outer insulative jaw housing 212, 222 disposed about the distal portion (not explicitly shown) of each jaw frame, and a tissue-treating plate 214, 224, respectively. The proximal flange portion (not shown) of jaw member 210 and proximal flange portion 221 of jaw member 220 are pivotably coupled to one another for moving jaw members 210, 220 between the spaced-apart position, first approximated position (FIG. 6B), and second approximated position (FIG. 7B). The distal portions of the jaw frames are configured to support jaw housings 212, 222, and tissue-treating plates 214, 224, respectively, thereon. Tissue-treating plates 214, 224 are formed from an electrically conductive material, e.g., for conducting electrical energy therebetween for treating tissue, similarly as detailed above. Further, tissue-treating plates 214, 224 may define serrated configurations to facilitate grasping and cutting of tissue, as detailed below.

One of the jaw members of end effector assembly 200, e.g., jaw member 220, defines a bifurcated configuration including first and second jaw components 220a, 220b. First and second jaw components 220a, 220b of jaw member 220 extend longitudinally in side-by-side relation relative to one another and each includes a tissue-treating plate portion 224a, 224b of tissue-treating plate 224. One or more biasing members 229 may be disposed between jaw components 220a, 220b to bias jaw components 220a, 220b towards one another, corresponding to the un-actuated condition of end effector assembly 200. As detailed below, when jaw members 210, 220 are moved to the second approximated position, jaw member 210 urges jaw components 220a, 220b apart from one another against the bias of biasing members 229, corresponding to the actuated condition of end effector assembly 200.

The other jaw member of end effector assembly 200, e.g., jaw member 210 includes a pair of spaced-apart, substantially planar tissue-contacting plate portions 214a, 214b that together define plate 214. Positioned between the spaced-apart plate portions 214a, 214b of jaw member 210 is an insulative member 218. More specifically, insulative member 218 extends longitudinally between plate portions 214a, 214b and towards jaw member 220. Insulative member 218 defines generally trapezoidal transverse cross-sectional configuration having angled sides 219a, 219b, although other configurations are also contemplated. Angled sides 219a, 219b permit the free end of insulative member 218 to extend partially between jaw components 220a, 220b of jaw member 220 in the first approximated position of end effector assembly 200 without effecting relative movement of jaw components 220a, 220b (the un-actuated condition of end effector assembly 200). However, upon further approximation of jaw members 210, 220, e.g., to the second approximated position, insulative member 218 extends further between jaw components 220a, 220b such that angled sides 219a, 219b urge jaw components 220a, 220b apart from one another against the bias of biasing member 229 (the actuated condition of end effector assembly 200).

In use, with end effector assembly 200 disposed in the un-actuated condition (FIGS. 6A and 6B) and jaw members 210, 220 disposed in the spaced-apart position, end effector assembly 200 is manipulated into position such that tissue to be treated and cut is disposed between jaw members 210, 220. With respect to tonsillectomy procedures, for example, end effector assembly 200 is positioned between the cavity wall tissue (or other tissue to remain) and the tonsil tissue (or other tissue to be removed). Once the desired position has been achieved, jaw members 210, 220 are moved to the first approximated position to grasp tissue between tissue-treating plates 214, 224 and, more specifically, between tissue-treating plate portions 214a, 214b and tissue-treating plate portions 224a, 224b, respectively. In the first approximated position, jaw components 220a, 220b of jaw member 220 are disposed in close proximity to one another such that plate portions 214a, 214b and plate portions 224a, 224b, respectively, are aligned with one another. Thereafter, tissue-treating plate portions 214a, 214b may be energized to a first electrical potential and tissue-treating plate portions 224a, 224b to a second, different electrical potential for conducting energy therebetween and through tissue grasped between jaw members 210, 220 to treat tissue.

Once tissue has been treated, the tissue to be removed, e.g., the tonsil tissue, is separated from the tissue to remain, e.g., the wall tissue. In order to separate the tissue, jaw members 210, 220 are moved from the first approximated position to the second approximated position such that insulative member 218 is advanced between jaw components 220a, 220b of jaw member 220 and urges jaw components 220a, 220b apart from one another to the actuated condition of end effector assembly 200. Movement of jaw components 220a, 220b to the actuated condition moves tissue-treating plate portions 224a, 224b apart from one another and relative to tissue-treating plate portions 214a, 214b such that the previously treated tissue grasped between jaw members 210, 220, which is substantially held in position via the serrated tissue-treating plate portions 214a, 214b and 224a, 224b, respectively, is cut in a dynamic shearing and/or ripping fashion, ultimately separating the tonsil tissue to be removed from the wall tissue to remain. The separated tonsil tissue may then be removed using end effector assembly 200, another grasping instrument, a suction device, or via other suitable method.

Turning to FIGS. 8A-9B, another embodiment of an end effector assembly is shown generally identified by reference numeral 300. End effector assembly 300 may be configured for use with forceps 10 (FIG. 1), forceps 10' (FIG. 2), or any other suitable surgical instrument, except that actuation assembly 60, 60' (FIGS. 1 and 2, respectively), need not be provided. Rather, similarly as with end effector assembly 200 (FIGS. 6A-7B), and as detailed below, end effector assembly 300 is configured for treating and cutting tissue by moving jaw members 310, 320 from a spaced-apart position to a first approximated position to grasp and treat tissue, and further to a second approximated position to cut tissue.

Each jaw member 310, 320 of end effector assembly 300 includes a jaw frame having a proximal flange portion 311, 321, an outer insulative jaw housing 312, 322 disposed about the distal portion (not explicitly shown) of each jaw frame, and a tissue-treating plate 314, 324, respectively. Proximal flange portions 311, 321 are pivotably coupled to one another about a pivot 303 for moving jaw members 310, 320 between the spaced-apart position, first approximated position (FIG. 8B), and second approximated position (FIG. 9B). The distal portions of the jaw frames are configured to support jaw housings 312, 322, and tissue-treating plates 314, 324, respectively, thereon. Tissue-treating plates 314, 324 are formed from an electrically conductive material, e.g., for conducting electrical energy therebetween for treating tissue, similarly as detailed above. Further, tissue-treating plates 314, 324 may define serrated configurations to facilitate grasping and cutting of tissue, as detailed below.

As mentioned above, proximal flange portions 311, 321 are pivotably coupled to one another about pivot 303. More specifically, proximal flange portions 311, 321 are disposed about pivot 303 with at least some play therebetween to permit one or both of proximal flange portions 311, 321 to move towards and away from the other along pivot 303. A biasing member 305 may be disposed about pivot 303 and coupled between proximal flange portions 311, 321 to bias proximal flange portions 311, 321 towards one another, thereby biasing jaw members 310, 320 towards an aligned configuration, corresponding to the un-actuated condition of end effector assembly 300. Biasing member 305 further serves to inhibit jaw splay during movement of jaw members 310, 320 between the spaced-apart position and the first approximated position.

Proximal flange portions 311, 321 of jaw members 310, 320 each further include an inwardly-extending protrusion 317, 327 defining a ramped surface 318, 328, respectively. Ramped surfaces 318, 328 are positioned to oppose one another and to slidably contact one another upon movement of jaw members 310, 320 from the first approximated position (FIG. 8A) to the second approximated position (FIG. 9A). More specifically, in the first approximated position, ramped surfaces 318, 328 are spaced-apart from one another (see FIG. 8A) and, as such, jaw members 310, 320 are biased to the aligned configuration, corresponding to the un-actuated condition of end effector assembly 300 (see FIG. 8B). Upon movement of jaw members 310, 320 to the second approximated position, ramped surfaces 318, 328 slidably contact one another and, due to the ramped configurations of protrusions 317, 327, increasingly urge proximal flange portions 311, 321 apart from one another (see FIG. 9A) to thereby move jaw members 310, 320 towards an offset configuration, corresponding to the actuated condition of end effector assembly 300 (see FIG. 9B).

In use, with end effector assembly 300 disposed in the un-actuated condition (FIGS. 8A and 8B) and jaw members 310, 320 disposed in the spaced-apart position, end effector assembly 300 is manipulated into position such that tissue to be treated and cut is disposed between jaw members 310, 320. With respect to tonsillectomy procedures, for example, end effector assembly 300 is positioned between the cavity wall tissue (or other tissue to remain) and the tonsil tissue (or other tissue to be removed). Once the desired position has been achieved, jaw members 310, 320 are moved to the first approximated position to grasp tissue between tissue-treating plates 314, 324. Thereafter, tissue-treating plate 314 may be energized to a first electrical potential and tissue-treating plate 324 to a second, different electrical potential for conducting energy therebetween and through tissue grasped between jaw members 310, 320 to treat, e.g., seal, tissue.

Once tissue has been treated, the tissue to be removed, e.g., the tonsil tissue, is separated from the tissue to remain, e.g., the wall tissue. In order to separate the tissue, jaw members 310, 320 are moved from the first approximated position to the second approximated position such that ramped surfaces 318, 328 slidably contact one another and urge proximal flange portions 311, 321 apart from one another to move jaw members 310, 320 to the actuated condition of end effector assembly 300. Movement of jaw members 310, 320 to the actuated condition moves tissue-treating plates 314, 324 relative to one another such that the previously treated tissue grasped between jaw members 310, 320, which is substantially held in position via the serrated tissue-treating plates 314, 324 is cut in a dynamic shearing and/or ripping fashion, ultimately separating the tonsil tissue to be removed from the wall tissue to remain. The separated tonsil tissue may then be removed using end effector assembly 300, another grasping instrument, a suction device, or via any other suitable method.

Figure 10A:
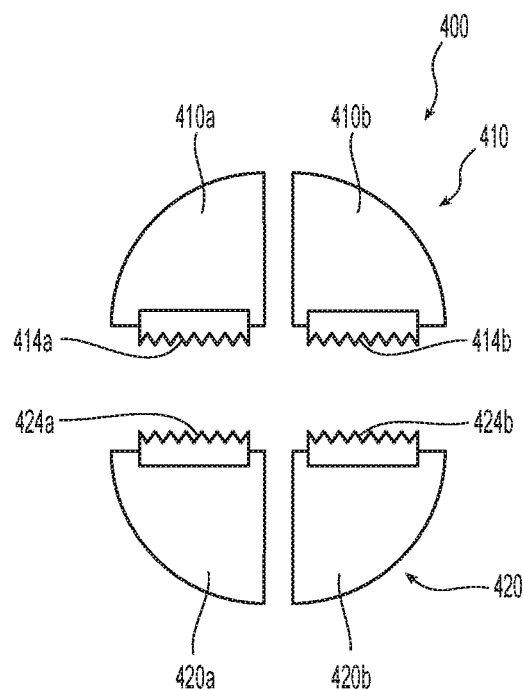
FIG. 10A is a transverse, cross-sectional view of the jaw bodies of another end effector assembly provided in accordance with the present disclosure, disposed in an un-actuated condition.
Figure 10B:
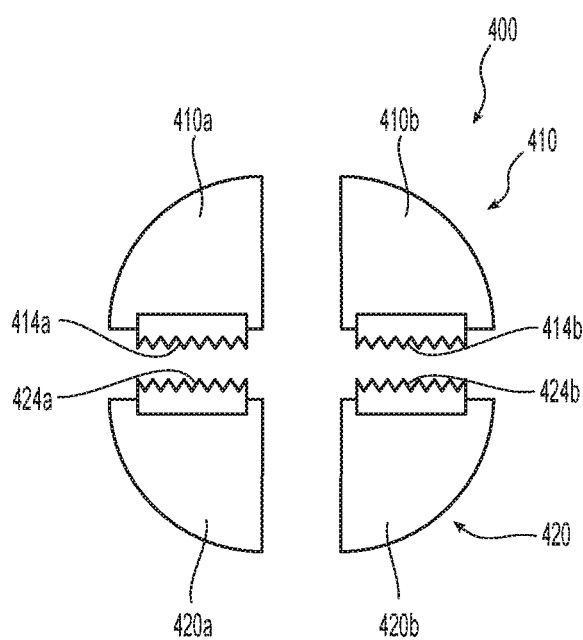
FIG. 10B is a transverse, cross-sectional view of the jaw bodies of the jaw members of the end effector assembly of FIG. 10A, disposed in an actuated condition.

Turning to FIGS. 10A and 10B, another embodiment of an end effector assembly is shown generally identified by reference numeral 400. End effector assembly 400 may be configured for use with forceps 10 (FIG. 1), forceps 10' (FIG. 2), or any other suitable surgical instrument. End effector assembly 400 is configured for treating and cutting tissue by moving jaw members 410, 420 from a spaced-apart position to an approximated position (FIG. 10A) to grasp and treat tissue, and then by moving each jaw member 410, 420 from an un-actuated position to an actuated position (FIG. 10B) to cut tissue. Movement between the spaced-apart and approximated positions may be accomplished via moving movable handle 40 of forceps 10 (FIG. 1) from the initial position to a first compressed position, while moving movable handle 40 (FIG. 1) from the first compressed position to a second compressed position may be effected to both move jaw members 410, 420 to a further approximated position and move of each of jaw members 410, 420 from the un-actuated position to the actuated position, similarly as with end effector assemblies 200 or 300 (FIGS. 6A-7B and FIGS. 8A-9B, respectively). Alternatively, with jaw members 410, 420 disposed in the approximated position, each jaw member 410, 420 may be moved from the un-actuated position to the actuated position via actuation of trigger 62 (FIG. 3A), similarly as with end effector assembly 100 (FIGS. 4A-5B).

Each jaw member 410, 420 of end effector assembly 400 defines a bifurcated configuration including first and second jaw components 410a, 410b and 420a, 420b, respectively. First and second jaw components 410a, 410b and 420a, 420b of respective jaw members 410, 420 extend longitudinally in side-by-side relation relative to one another and each includes a tissue-treating plate portion 414a, 414b and 424a, 424b that cooperate to define the tissue-treating plates of jaw members 410, 420. Tissue-treating plate portions 414a, 414b and 424a, 424b are formed from an electrically conductive material, e.g., for conducting electrical energy therebetween for treating tissue, similarly as detailed above. Further, tissue-treating plate portions 414a, 414b and 424a, 424b may define serrated configurations to facilitate grasping and cutting of tissue, as detailed below.

As noted above, jaw members 410, 420 of end effector assembly 400 are configured to move between a spaced-apart position and an approximated position (FIG. 10A), and each jaw member 410, 420, with the jaw members 410, 420 disposed in the approximated position (FIG. 10A), is further configured to move between an un-actuated position (FIG. 10A) and an actuated position (FIG. 10B). As also noted above, in some embodiments, the actuated position of each of jaw members 410, 420 corresponds to a further approximated position of jaw members 410, 420. In either configuration, in the un-actuated position, jaw components 410a, 410b of jaw member 410 are positioned adjacent one another in close proximity to one another and, similarly, jaw components 420a, 420b of jaw member 420 are positioned adjacent one another in close proximity to one another. Upon movement of jaw members 410, 420 to the actuated position, jaw components 410a, 410b of jaw member 410 are moved apart from one another and, similarly, jaw components 420a, 420b of jaw member 420 are moved apart from one another.

In use, with jaw members 410, 420 initially disposed in the spaced-apart position, end effector assembly 400 is manipulated into position such that tissue to be treated and cut is disposed between jaw members 410, 420. With respect to tonsillectomy procedures, for example, end effector assembly 400 is positioned between the cavity wall tissue (or other tissue to remain) and the tonsil tissue (or other tissue to be removed). Once the desired position has been achieved, jaw members 410, 420 are moved to the approximated position to grasp tissue between the tissue-treating plate portions 414a, 414b of jaw member 410 and the tissue-treating plate portions 424a, 424b of jaw member 420. More specifically, a first portion of tissue is grasped between tissue-treating plate portions 414a, 424a and a second portion of tissue is grasped between tissue-treating plate portions 414b, 424b.

Thereafter, tissue-treating plate portions 414a, 414b may be energized to a first electrical potential and tissue-treating plate portions 424a, 424b to a second, different electrical potential for conducting energy therebetween and through tissue grasped between jaw members 410, 420 to treat tissue. More specifically, both the first portion of tissue grasped between tissue-treating plate portions 414a, 424a and a second portion of tissue grasped between tissue-treating plate portions 414b, 424b are treated via the conduction of energy therethrough.

Once tissue has been treated, the tissue to be removed, e.g., the tonsil tissue, is separated from the tissue to remain, e.g., the wall tissue. In order to separate the tissue, jaw members 410, 420 are moved from the un-actuated position to the actuated position such that jaw components 410a, 420a are moved apart from respective jaw components 410b, 420b. Thus, as jaw members 410, 420 are moved from the un-actuated position to the actuated position, the first and second portions of previously-treated tissue are pulled apart from one another, ultimately such that the tissue disposed therebetween is ripped and/or torn, separating the first and second portions of previously-treated tissue from one another. With respect to tonsillectomy procedures, for example, moving jaw members 410, 420 from the un-actuated position to the actuated position separates the tonsil tissue to be removed from the wall tissue to remain. The separated tonsil tissue (or other tissue) may then be removed using end effector assembly 400, another grasping instrument, a suction device, or via other suitable method.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
an end effector assembly including first and second jaw members each including at least one tissue-treating plate having a planar configuration across a width thereof defined perpendicular to a longitudinal axis of the end effector assembly, wherein the first and second jaw members each define a lateral surface, and wherein the first and second jaw members are relatively movable between:
a spaced-apart position;
a first approximated position, wherein each of the at least one tissue-treating plates of the first jaw member is substantially parallel and aligned with a corresponding one of the at least one tissue-treating plates of the second jaw member and defines a first gap distance therebetween; and
a second approximated position, wherein each of the at least one tissue-treating plates of the first jaw member is substantially parallel and laterally offset relative to the corresponding one of the at least one tissue-treating plates of the second jaw member and defines a second, smaller gap distance therebetween,
wherein at least one of the first or second jaw members is moved vertically to effect the relative movement between the spaced-apart position and the first approximated position, and wherein at least one of the first or second jaw members is moved laterally to effect the relative movement between the first approximated position and the second approximated position;
a first protrusion extending from the first jaw member, the first protrusion defining a first ramped surface; and a second protrusion extending from the second jaw member, the second protrusion defining a second ramped surface directly contacting the first ramped surface, the first and second ramped surfaces configured to urge the first and second jaw members laterally during the relative movement of the first and second jaw members between the first approximated position and the second approximated position, wherein vertical movement of the first and second jaw members from the first approximated position to the second approximated position causes the lateral surfaces of the first and second jaw members to move laterally away from each other.

2. The surgical instrument according to claim 1, wherein each of the first and second jaw members includes:
   a jaw body having the at least one tissue-treating plate disposed thereon; and
   a proximal flange.

3. The surgical instrument according to claim 2, wherein the proximal flange of each of the first and second jaw members includes one of the protrusions disposed thereon, and wherein, during the relative movement of the first and second jaw members from the first approximated position to the second approximated position, the protrusions contact one another and urge the proximal flanges apart from one another, thereby urging the at least one of the first or second jaw members to move laterally.

4. The surgical instrument according to claim 2, wherein the proximal flanges of the first and second jaw members are pivotably coupled to one another to permit pivotal vertical movement of the at least one of the first or second jaw members.

5. The surgical instrument according to claim 1, wherein the at least one tissue-treating plate of each of the first and second jaw members defines a serrated configuration to facilitate grasping and cutting of tissue.

6. The surgical instrument according to claim 1, further including an actuation assembly operably coupled to the at least one protrusion, the actuation assembly including an actuation member movable between a first position and a second position to move the at least one protrusion.

7. The surgical instrument according to claim 6, wherein the actuation assembly includes a trigger coupled to the actuation member, the trigger selectively actuatable for moving the actuation member between the first position and the second position.

8. The surgical instrument according to claim 1, wherein each of the at least one tissue-treating plates of the first and second jaw members is adapted to connect to a source of energy for conducting energy through tissue.

* * * * *